United States Patent [19]

Crooms

[11] 4,414,720
[45] Nov. 15, 1983

[54] CRANIAL CLOSURE

[76] Inventor: Clarence Crooms, 19144 Coyle, Detroit, Mich. 48235

[21] Appl. No.: 400,809

[22] Filed: Jul. 22, 1982

[51] Int. Cl.³ ............................................. A01N 1/00
[52] U.S. Cl. ...................................................... 27/21
[58] Field of Search ............... 27/21; 128/92 R, 92 A, 128/92 B, 92 D

[56] References Cited

U.S. PATENT DOCUMENTS

| | | | |
|---|---|---|---|
| 2,061,550 | 11/1936 | Cavazza | 27/21 |
| 2,162,612 | 6/1939 | Ebert | 27/21 |
| 2,587,292 | 2/1952 | De Voe | 27/21 |
| 3,205,553 | 9/1965 | Pfeifer | 27/21 |
| 4,240,186 | 12/1980 | Rector | 27/21 |

*Primary Examiner*—John D. Yasko

*Attorney, Agent, or Firm*—Cullen, Sloman, Cantor, Grauer, Scott & Rutherford

[57] ABSTRACT

A cranial closure for an embalming incision includes an elongated resilient metallic strip formed into U-shape. A plurality of spaced opposed pairs of tines project from opposite sides of the strip and extend radially inward at right angles thereto. A pair of laterally spaced opposed rows of longitudinally spaced spikes extend from the strip radially inward thereof and inwardly of the tines. The strip is adapted to overlie, span and extend along the incision with the spikes retainingly extending through opposed registering skin sections adjacent the incision for closing the incision, the tines retainingly projecting through the skin sections and adjacent sub tissue for anchoring the strip to the cranium.

2 Claims, 5 Drawing Figures

CRANIAL CLOSURE

BACKGROUND OF THE INVENTION

Heretofore in the performance of embalming the incision in the human cranium or scalp heretofore has been closed by stitching which is difficult and time consuming.

SUMMARY OF THE INVENTION

The primary feature of the present invention is to provide a cranial closure which is adapted to overlie, span and extend along such incision. The strip defining the closure has formed therein a pair of laterally spaced rows of longitudinally spaced spikes which are struck from the strip extend radially inward thereof and are adapted to retainingly engage adjacent drawn up skin sections as a result of the incision holding the skin sections together for closing such incision. A further feature includes formed from the strip a series of opposed pairs of longitudinally spaced tines which extend from the edges of the strip at right angles to the strip which are adapted to extend through and retainingly engage skin sections and adjacent sub tissue anchoring the strip to the cranium.

A further feature resides in the formation of a unit cranial closure made from steel or other metal which as a unit part thereof includes opposed pairs of radial spikes arranged in rows adapted for piercing and gripping and holding together drawn up tissue elements adjacent the incision and wherein the strip includes along opposite edges a plurality of longitudinally spaced pairs of pointed tines which also extend at right angles to the body of the strip and are adapted to pierce the scalp, the skin tissue elements and underlying tissue for anchoring the strip to the cranium.

A further feature incorporates the formation of the present cranial closure from a unit strip. This can be formed to the correct arcuate shape and wherein the tines and spikes are integral with the strip and formed in a stamping or punching operation.

These and other objects will be seen from the following specification and claims in conjunction with the appended drawing.

THE DRAWING

It will be understood that the above drawing illustrates merely a preferred embodiment of the invention and mode of use, and that other embodiments are contemplated in the scope of the claims thereto set forth.

DETAILED DESCRIPTION OF AN EMBODIMENT OF THE INVENTION

Figure 1:
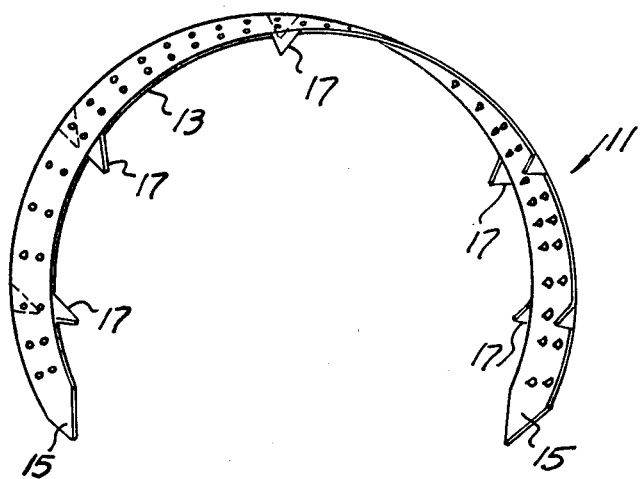
FIG. 1 is a perspective view of the present cranial closure.

Referring to the drawing, the present cranial closure of general U-shape, or arcuate is designated at 11 in FIG. 1. The closure includes an elongated strip 13 of metal, such as stainless steel or steel whose opposite ends are tapered as at 15.

Figure 3:
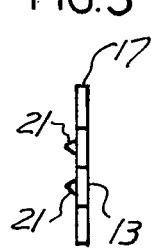
FIG. 3 is an end elevational view thereof.
Figure 2:
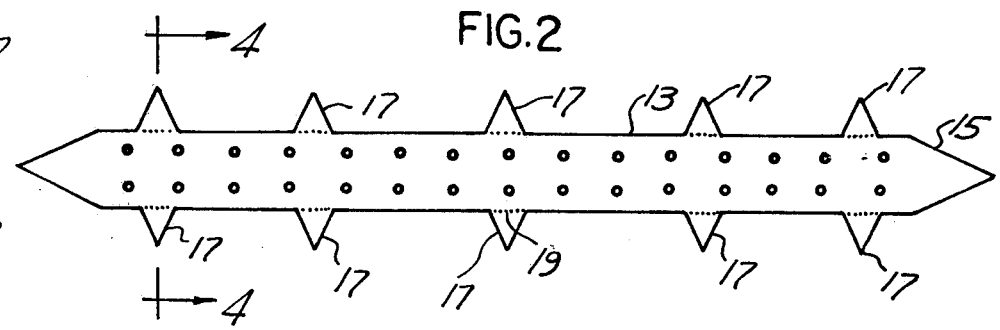
FIG. 2 is a plan view of an elongated metallic strip defining said cranial closure before forming into arcuate shape.

As shown in FIGS. 2 and 3 the strip when formed includes a plurality of longitudinally spaced opposed pairs of tapered tines 17 pointed at their ends which initially project laterally of the strip coplanar therewith.

Figure 4:
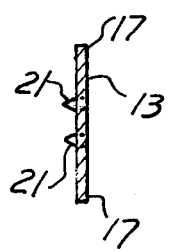
FIG. 4 is a section taken in the direction of arrows 4—4 of FIG. 2.

There is formed by striking out or punching or otherwise through the strip 13 a pair of laterally spaced rows of longitudinally spaced skin section retaining spikes 21 which are pointed at their ends and which extend generally radially inward of the strip at right angles thereto, FIG. 4.

Figure 5:
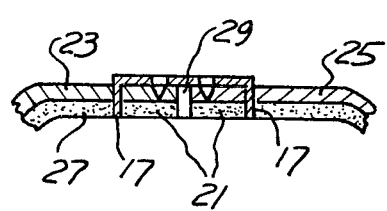
FIG. 5 is a schematic view, similar to FIG. 4 showing the strip as overlying the incision in the cranium with the spikes retainingly engaging scalp tissue adjacent the incision on opposite sides thereof and with respective tines retainingly projected through the adjacent tissue and sub tissue for anchoring the strip to the cranium.

A further step in the construction of the present cranial closure is the bending of the respective tines 17 such as along the score or fold lines 19 so as to extend at right angles to the strip as shown in FIGS. 4 and 5.

The present strip is sufficiently resilient so as to conform to the particular shape of a cranium which would normally have formed therethrough transverse incision 29, FIG. 5 for the purpose of embalming. Such incision defines within the scalp of the cranium a pair of opposed adjacent skin sections 23 and 25 with adjacent and severed sub tissue 27 shown schematically in FIG. 5.

In use of the present cranial closure, the skin sections on opposite sides of and adjacent to the incision 29 are substantially drawn together manually and the arcuate strip is applied to the scalp so as to span and extend along the incision longitudinally thereof so that the internal rows of spikes 21 pierce and retainingly engage adjacent inner portions of the skin sections substantially closing the incision 29. At the same time, inturned or radial tines 17 retainingly project through said skin sections and through the adjacent sub tissue 27 by which the strip defining the cranial closure is secured to outer surface portions of the cranium or scalp.

The present cranial closure is inexpensive to manufacture and is made in one piece and is of sufficient flexibility as to conform to the curvature or shape of a particular cranium as it is used to overlie the embalming incision therein and for the purpose of drawing together the skin sections of the scalp adjacent the incision closing such incision and wherein the adjacent sections of the scalp are retained together by the spikes 21 and wherein opposed tines 17 retainingly project through the skin sections and adjacent sub tissue for the purpose of anchoring the closure to the cranium.

Having described my invention reference should now be had to the following claims.

I claim:

1. A cranial closure comprising an elongated flexible metallic strip having a pair of opposing side edges and formed into U-shape between its ends;

a plurality of longitudinally spaced opposed pairs of tapered tines projecting from said side edges and extending radially inward at right angles to said strip along its length and upon opposite sides thereof;

and a pair of laterally spaced rows of longitudinally spaced skin retaining spikes struck from said strip and extending radially inward thereof parallel to said tines;

said strip adapted to overlie, span and extend along an incision of the cranium resulting from embalming, creating opposed registering skin sections of the scalp adjacent said incision and including sub tissue;

the spikes retainingly extending through opposed registering portions of said skin sectins holding them substantially drawn together to close said incision, said tines retainingly projecting through adjacent skin sections and adjacent sub tissue for anchoring said strip upon said cranium;

said strip being arcuate for substantial cooperative registry with the cranium, said tines and spikes being pointed;

said tines being longer than said spikes with the respective ends extending radially outward thereof.

2. In the cranial closure of claim 1, the ends of said strip being tapered.

* * * * *